US00PP29541P3

(12) United States Plant Patent
Suphachadiwong

(10) Patent No.: US PP29,541 P3
(45) Date of Patent: Jul. 24, 2018

(54) ***VANDA* PLANT NAMED 'SPCDW1513'**

(50) Latin Name: ***Vanda* Jones ex R. Br.**
Varietal Denomination: SPCDW1513

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 54 days.

(21) Appl. No.: 15/330,347

(22) Filed: Sep. 9, 2016

(65) Prior Publication Data

US 2017/0079175 P1 Mar. 16, 2017

(30) Foreign Application Priority Data

Sep. 15, 2015 (QZ) ..... PBR 2015/2162

(51) Int. Cl.
*A01H 5/02* (2018.01)

(52) U.S. Cl.
USPC ..... Plt./311

(58) Field of Classification Search
USPC ..... Plt./311
See application file for complete search history.

*Primary Examiner* — Keith O Robinson
(74) *Attorney, Agent, or Firm* — Samuel R. McCoy

(57) ABSTRACT

A new and distinct *Vanda* cultivar named 'SPCDW1513' which is characterized by violet sepals and petals which fade to a darker violet along the margins and apex, sepals and petals that exhibit a dark violet irregular tessellation pattern, a labellum with purple-violet lateral lobes that are blotched red-purple at the base and a dark violet central lobe, as well as the stability of these characteristics from generation to generation.

4 Drawing Sheets

Latin name of the genus and species: The Latin name of the genus and species of the novel variety disclosed herein is *Vanda* Jones ex R. Br.

Variety denomination: The inventive variety of *Vanda* disclosed herein has been given the variety denomination 'SPCDW1513'.

CROSS REFERENCE TO RELATED APPLICATIONS

This application claims priority to the Community Plant Variety Rights application number 2015/2162, filed Sep. 15, 2015, which is herein incorporated by reference.

BACKGROUND OF THE INVENTION

Parentage: The *Vanda* variety 'SPCDW1513' is the result of a planned breeding program. The new variety originated as a seedling from the crossing of an unnamed *Vanda* seed parent (not patented) with an unnamed *Vanda* pollen parent (not patented). Both parents were developed by, and are owned by, the inventor and were never commercially released. The crossing was made by the inventor in his research greenhouse in Bangphra, Thailand in February of 1988.

The new variety was first selected in November of 1992, in a research greenhouse in Bangphra, Thailand belonging to the inventor. After identifying the new variety as a potentially interesting selection, the inventor continued confidential testing and propagation of 'SPCDW1513', assessing stability of the unique characteristics of this variety.

Asexual Reproduction: Asexual reproduction of the new cultivar 'SPCDW1513', by way of mericloning, was first initiated in November of 2009 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1513' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1513'. These characteristics in combination distinguish 'SPCDW1513' as a new and distinct *Vanda* cultivar:

1. *Vanda* 'SPCDW1513' exhibits sepals and petals which are violet and fading darker along the margins and apex; and
2. *Vanda* 'SPCDW1513' exhibits sepals with a prominent darker violet irregular tessellation pattern; and
3. *Vanda* 'SPCDW1513' exhibits a labellum with purple-violet lateral lobes which are blotched red-purple at the base, and a dark violet central lobe.

BOTANICAL DESCRIPTION OF THE PLANT

Figure 1:
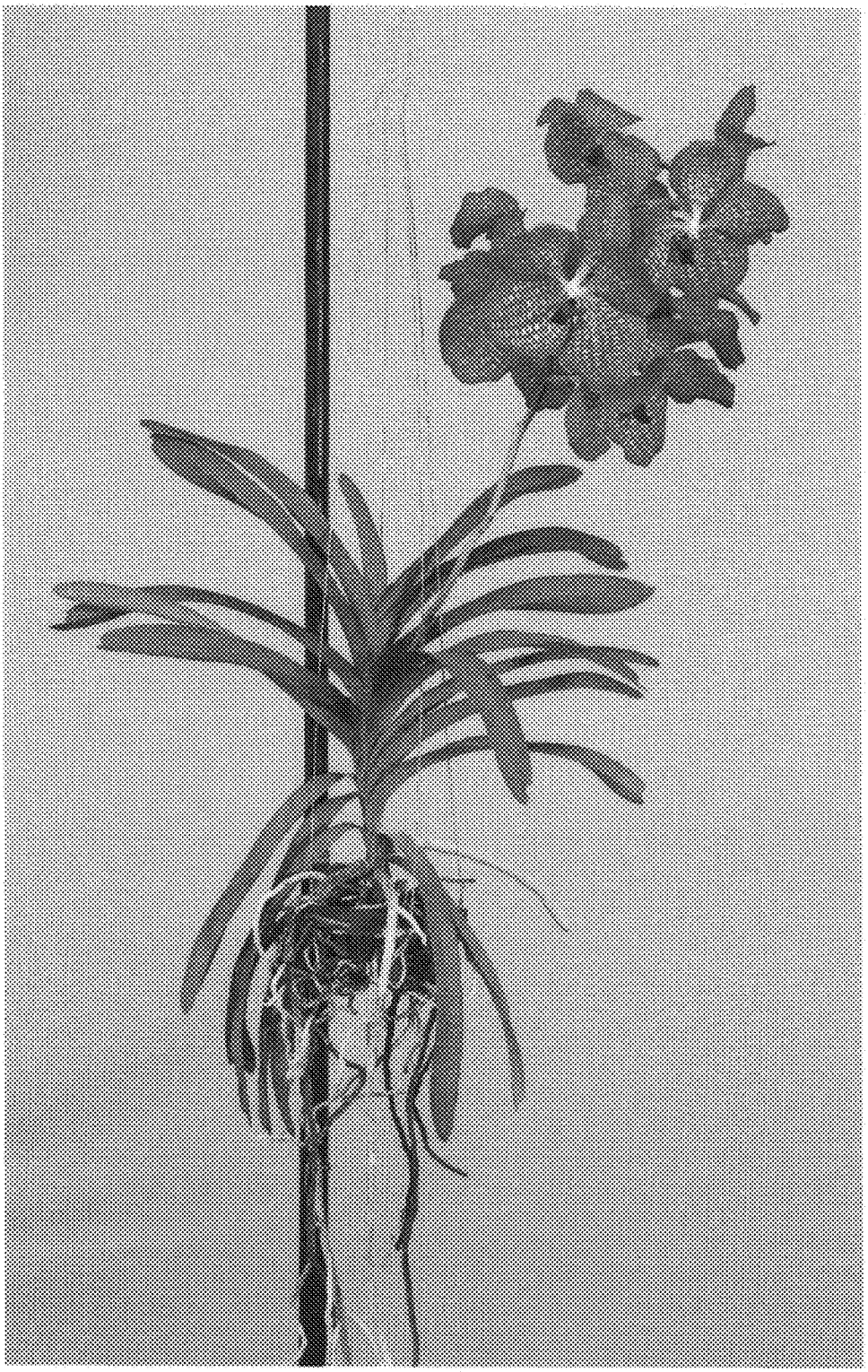
FIG. 1 illustrates, as nearly true as it is reasonably possible to make the same in color photographs of this type, an exemplary plant of 'SPCDW1513' grown in a commercial greenhouse in Honselersdijk, the Netherlands. This plant is approximately 6 years old from the time of mericloning, shown planted in an 8 by 8 cm container.
Figure 2:
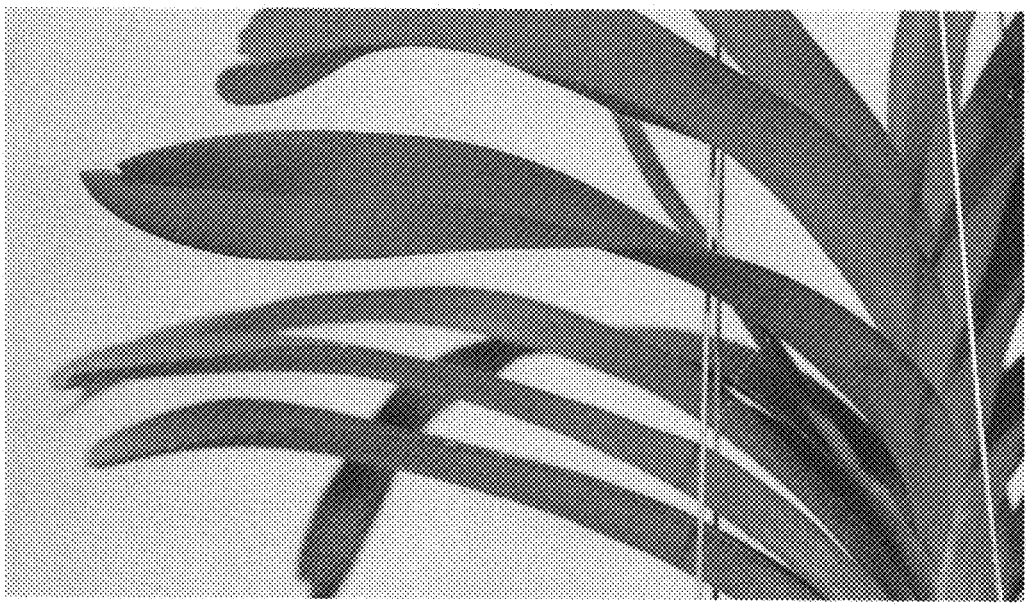
FIG. 2 illustrates, as nearly true as it is reasonably possible to make the same in color photographs of this type, the typical foliage of 'SPCDW1513'.
Figure 3:
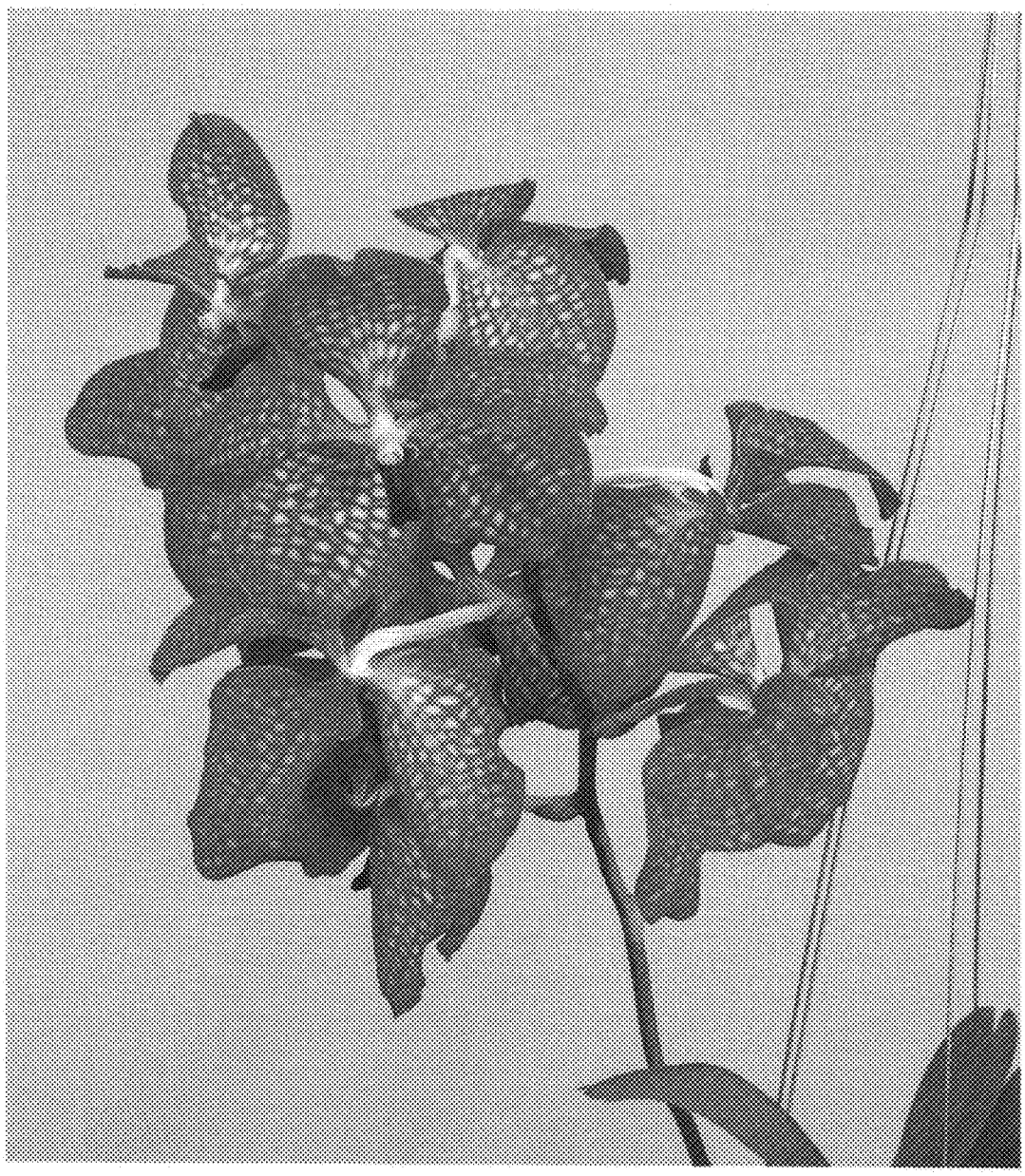
FIG. 3 illustrates, as nearly true as it is reasonably possible to make the same in color photographs of this type, the typical inflorescence of 'SPCDW1513'.
Figure 4:
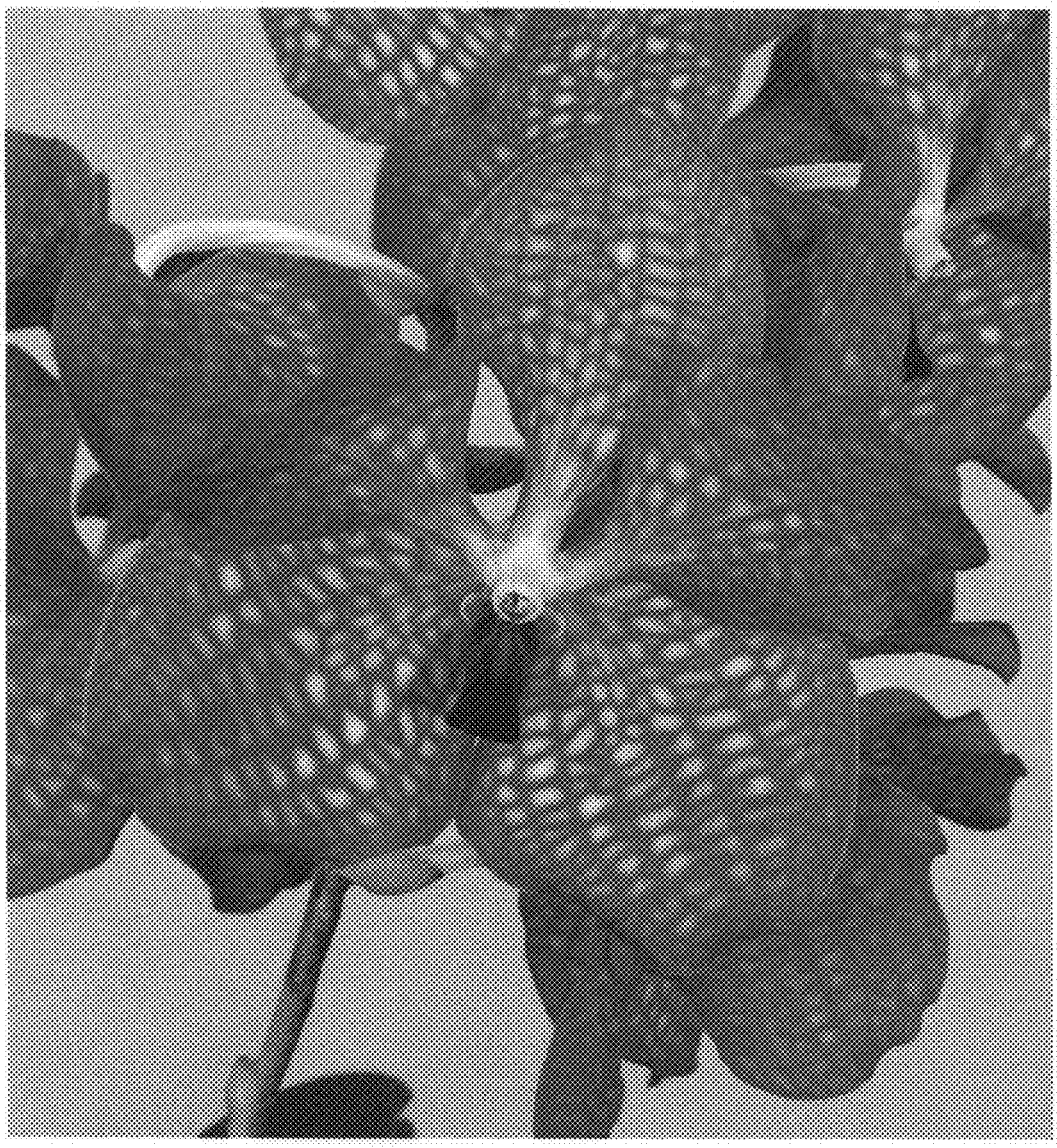
FIG. 4 illustrates, as nearly true as it is reasonably possible to make the same in color photographs of this type, the typical flower of 'SPCDW1513'.

The following observations and measurements made in August of 2016 describe averages from a sample set of six specimens of six year-old 'SPCDW1513' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1513' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'SPCDW1513' and comparisons with other varieties of *Vanda* are provided below.

Plant description:

- *Growth habit.*—Perennial; monopodial, upright. Single monopodial leafy stem, with flowers carried above the leaf plane with inflorescences growing from the leaf axils.
- *Average height from base (plant grown in hanging basket, so no soil line present) to foliar plane.*—33.1 cm.
- *Average height from base (plant grown in hanging basket, so no soil line present) to top of floral plane.*—58.3 cm.
- *Plant spread.*—Average of 40.3 cm.
- *Appropriate container size.*—8 cm by 8 cm rectangular hanging basket.
- *Growth rate.*—Moderate.
- *Plant vigor.*—Moderate.
- *Propagation type.*—Tissue culture propagation using the base of the leaves.
- *Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility.*—Plants have not been observed to be susceptible or resistant to pathogens and pests common to *Vanda.*
- *Environmental tolerances.*—Adapt to, at least, USDA Zones 11 and 12 and temperatures as high as 40 degrees Celsius; high tolerance to rain; moderate to high tolerance to wind.

Root system:

- *General.*—Densely rooting; with aerial roots only.
- *Dimensions, mature roots.*—57.6 cm long with a diameter of 0.5 cm, on average.
- *Texture.*—Very fleshy; non-fibrous.
- *Color.*—Greyed-Green, near RHS 192A to 192B; root apex is yellow-green, RHS 146A.

Stem:

- *Branching habit.*—Monopodial; no lateral branches present.
- *Number of primary (main) stems per plant.*—One.
- *Number of secondary (lateral) branches per plant.*—None.
- *Appearance and shape.*—Circular, formed by the leaf sheaths.
- *Length.*—21.0 cm.
- *Diameter.*—0.7 cm.
- *Internode length.*—0.8 cm.
- *Luster.*—Matte.
- *Aspect.*—Near vertical.
- *Strength.*—Very strong.
- *Color, juvenile.*—Yellow-green, near RHS 145D.
- *Color, mature.*—Yellow-green, near RHS 145D.
- *Color at internodes.*—Yellow-green, near RHS 145D.
- *Pubescence.*—Glabrous.

Foliage:

- *Arrangement.*—Distichous.
- *Dimensions.*—23.8 cm long and 2.5 cm wide, on average.
- *Shape of blade.*—Ligulate; moderately carinate.
- *Aspect.*—Moderately curved.
- *Apex.*—Unequal praemorse.
- *Base.*—Sheathing.
- *Sheath dimensions.*—3.1 cm long and 1.1 cm wide, on average.
- *Sheath color.*—Yellow-green, near RHS 145B.
- *Margin.*—Entire.
- *Pubescence, texture and luster of adaxial surface.*—Glabrous, smooth, and very slightly glossy.
- *Pubescence, texture and luster of abaxial surface.*—Glabrous, smooth, and matte.
- *Color.*—Variegation — Absent. Foliar spots, adaxial surface — Absent. Juvenile foliage, adaxial surface — In between green, near RHS 143B, and yellow-green, near RHS 144A. Juvenile foliage, abaxial surface — Green, near RHS 143A to 143B. Mature foliage, adaxial surface — Green, near RHS 143A. Mature foliage, abaxial surface — Yellow-green, near RHS 144A.
- *Venation.*—Parallel.
- *Venation color, adaxial surface.*—Green, near RHS 143A.
- *Venation color, abaxial surface.*—Yellow-green, RHS 144A.
- *Petiole.*—No petioles present; leaves sessile.

Inflorescence:

- *Inflorescence arrangement.*—Axially placed raceme.
- *Natural flowering season.*—Autumn into winter.
- *Time to flower.*—Approximately 10 months.
- *Quantity of inflorescence per plant.*—One.

*Flowers per inflorescence.*—Average of 10; 9 open flowers and 1 bud.

*Inflorescence height.*—Approximately 24.5 cm (measured from base of lowest flower to top of upper flower).

*Inflorescence diameter.*—Approximately 21.2 cm.

*Peduncle.*—Dimensions — Approximately 41.0 cm long and 0.5 cm wide. Aspect — Generally at a 30 degree angle to lateral branch axis, varying between 25 and 35 degrees. Strength — Moderately strong. Texture and luster — Glabrous and moderately glossy. Color — Green, near RHS 143B to 143C.

Bud:

*Length.*—Average of 1.5 cm.

*Diameter.*—Average horizontal diameter is 1.4 cm; the vertical diameter is 1.8 cm.

*Shape.*—Cubic, with a deltoid apex which is pointed downward.

*Pubescence, texture and luster.*—Glabrous, smooth and matte.

*Color.*—Yellow-green, near RHS 145C to 145D; apex is violet, near RHS 86D.

Flower:

*Flower type.*—Zygomorphic (orchidaceous), typical shape for the genus *Vanda*.

*Flowering habit.*—Moderate.

*Shape.*—Zygomorphic, single; consisting of three sepals and three petals, one of which is transformed into a labellum.

*Aspect.*—Flowers are outward-facing to slightly nodding.

*Vertical height.*—Approximately 11.9 cm.

*Diameter.*—Approximately 11.8 cm.

*Depth.*—Approximately 4.6 cm.

*Fragrance.*—No fragrance.

*Lastingness.*—3 weeks, on average.

*Persistent.*—Self-cleaning.

*Petals.*—Quantity of Petals — Three unfused petals; two conventional petals and one labellum. Arrangement — One lateral petal on each side. Length — Approximately 6.1 cm. Width — Approximately 5.3 cm. Shape — Broad ovate; broadest at the middle of the petal. Apex — Obtuse. Base — Cuneate. Margin — Entire; moderately undulated. Pubescence, texture and luster of upper surface — Glabrous, velvety and matte. Pubescence, texture and luster of lower surface — Glabrous, velvety and matte. Color when opening, upper surface — Violet, near RHS 85C to 85D, with darker reticulate veining, near RHS N88B. Color when opening, lower surface — Violet, near RHS 85D, with darker reticulate veining, in between near RHS N87A and N88B. Color when fully opened, upper surface — Violet, lighter than near RHS N87D, and fading darker, near RHS N87C to N87D. Color when fully opened, lower surface — Violet, lighter than near RHS N87D, and fading darker, near RHS N87C. Fading, upper surface — Not fading. Fading, lower surface — Not fading. Venation — Densely reticulate. Venation color, fully opened, upper surface — Violet, in between near RHS N87A and N88A. Venation color, fully opened, lower surface — Violet, in between near RHS N87A and N88A to N88B.

*Labellum.*—Shape — Three-lobed, lateral lobes are involute and the central lobe is revolute. Whiskers are absent. Length — Central lobe — Approximately 2.3 cm. Lateral lobes — Approximately 1.0 cm. Width — Central lobe — Approximately 1.1 cm. Lateral lobes — Approximately 0.7 cm. Apex, central and lateral lobes — Emarginate. Base, central and lateral lobes — Cuneate. Margin, central lobe — Entire; revolute and slightly undulate. Margin, lateral lobes — Entire; no undulation. Texture and luster of upper surface — Central lobe — Glabrous, velvety, and matte. Lateral lobes — Glabrous, velvety, and matte. Texture and luster of lower surface — Central lobe — Glabrous, velvety, and very slightly glossy. Lateral lobes — Glabrous, velvety, and matte. Color when opening, upper surface — Central lobe — Violet, near RHS 83B, and fading to violet-blue at the top, in between near RHS 83A and N92D. Lateral lobes — Purple-violet, near RHS N80C to N80D; blotched red-purple at the base, RHS 72B. Color when opening, lower surface — Central lobe — Violet, near RHS 86A, and fading to purple-violet towards the base, near RHS N82C. Lateral lobes — Purple-violet, near RHS N82D; margined darker, near RHS N82A. Color when fully opened, upper surface — Central lobe — Violet, near RHS 86B, and fading to violet at the top, in between near RHS N92B to N92C. Lateral lobes — Purple-violet, near RHS N80C to N80D; blotched red-purple at the base, RHS 72B. Color when fully opened, lower surface — Central lobe — Violet, darker than near 86A, and fading lighter towards the base, near RHS 86C to 86D. Lateral lobes — Purple-violet, near RHS N82D, and margined darker, near N82A. Fading, upper surface — Not fading. Fading, lower surface — Not fading. Venation — Densely reticulate. Venation color, fully opened, upper surface — Central lobe — Violet, near RHS 86B, and fading to violet at the top, near RHS N92B to N92C. Lateral lobes — Purple-violet, near RHS N80C to N80D; blotched red-purple at the base, RHS 72B. Venation color, fully opened, lower surface — Central lobe — Violet, darker than near 86A, and fading lighter towards the base, near RHS 86C to 86D. Lateral lobes — Purple-violet, near RHS N82D; margined darker, near RHS N82A.

*Callosities.*—Dimensions — 1.4 cm long and 0.8 cm wide, on average. Color — Violet, near RHS 86B.

*Spurs.*—Quantity — Average of 1. Length — Approximately 0.9 cm. Diameter — Approximately 0.3 cm. Vertical height — Approximately 0.6 cm, at the base. Shape — Short triangular. Apex — Bluntly acute. Base — Broad Cuneate. Pubescence, texture and luster — Glabrous, smooth, and matte. Color — Violet, near RHS 85C, and slightly striped darker, near RHS 85A.

*Sepals.*—Quantity — Average of 3 unfused sepals. Arrangement — One dorsal sepal and two lateral sepals. Length — Dorsal sepal — Approximately 6.2 cm. Lateral sepals — Approximately 6.6 cm. Width — Dorsal sepal — Approximately 5.0 cm. Lateral sepals — Approximately 6.0 cm. Shape — Dorsal sepal — Broad ovate to broad oblong. Lateral sepals — Broad ovate. Apex, dorsal and lateral sepals — Obtuse. Base, dorsal and lateral sepals — Cuneate. Margin, dorsal and lateral sepals — Entire;

moderately undulated. Pubescence, texture and luster — Glabrous, velvety, and matte on both the upper and lower sepal surfaces. Color when opening, upper surface — Dorsal sepal — Violet, near RHS 85C to 85D, with darker reticulate veining, near RHS N88B. Lateral sepals — Violet, near RHS 85C to 85D, with darker reticulate veining, near RHS N88B. Color when opening, lower surface — Dorsal sepal — Violet, near RHS 85D, with darker reticulate veining, in between near RHS N87A and N88B. Lateral sepals — Violet, near RHS 85D, with darker reticulate veining, in between near RHS N87A and N88B. Color when fully opened, upper surface — Dorsal sepal — Violet, lighter than near RHS N87D, and fading darker, near N87C to N87D. Lateral sepals — Violet, lighter than near RHS N87D, and fading darker, near N87C to N87D. Color when fully opened, lower surface — Dorsal sepal — Violet, lighter than near RHS N87D, and fading darker, near RHS N87C. Lateral sepals — Violet, lighter than near RHS N87D, and fading darker, near RHS N87C. Fading, upper surface — Not fading. Fading, lower surface — Not fading. Venation — Densely reticulate. Venation color, fully opened, upper surface — Dorsal sepal — Violet, in between near RHS N87A and N88A. Lateral sepals — Violet, in between near RHS N87A and N88A. Venation color, fully opened, lower surface — Dorsal sepal — Violet, in between near RHS N87A and N88A and N88B. Lateral sepals — Violet, in between near RHS N87A and N88A and N88B.

*Pedicels.*—Length — Approximately 6.4 cm. Diameter — Approximately 0.5 cm. Angle — Approximately 75 degree angle to peduncle axis, varying between 70 and 80 degrees. Strength — Moderate. Texture — Glabrous, axially angled with 5 "ribs", axially twisted (due to resupination). Luster — Glossy. Color — Violet, near RHS 85C to 85D.

*Bract.*—Quantity — One bract present at the base of each pedicel. Shape — Broad ovate; folded around the base of each pedicel. Dimensions — Average of 1.6 cm long and 1.5 cm wide. Apex — Obtuse. Base — Broad cuneate. Margins — Entire.

Reproductive organs:

*Column.*—Length — Approximately 0.6 cm. Diameter — Approximately 0.7 cm. Color — White, RHS NN155D, and tinged purple-violet, RHS N82D.

*Ovary.*—Position — Inferior. Diameter — Approximately 0.3 cm. Color — Yellow green, RHS 150C.

*Pollinia color.*—Yellow-orange, RHS 14A.

Seed and fruit: No fruit and seed production has been detected to date.

Comparison with the parent plants: Plants of the new cultivar 'SPCDW1513' differ from the unnamed *Vanda* seed parent (not patented) by the characteristics described in Chart 1.

CHART 1

| Characteristic | 'SPCDW1513' | Unnamed seed parent |
|---|---|---|
| Flower color. | Background color is violet. | Background color is purple. |
| Flower color pattern. | Tessellated. | No tessellation. |
| Inflorescence. | Racemes are longer than those of the seed parent. | Racemes are shorter than those of 'SPCDW1513'. |

CHART 1-continued

| Characteristic | 'SPCDW1513' | Unnamed seed parent |
|---|---|---|
| Plant size. | Larger than the seed parent. | Smaller than 'SPCDW1513'. |
| Plant vigor. | More vigorous; faster growing when compared to the seed parent. | Less vigorous; slower growing than 'SPCDW1513'. |

Plants of the new cultivar 'SPCDW1513' differ from the unnamed *Vanda* pollen parent (not patented) by the characteristics described in Chart 2.

CHART 2

| Characteristic | 'SPCDW1513' | Unnamed pollen parent |
|---|---|---|
| Flower color. | Violet. | Dark blue. |
| Color pattern on the petals and sepals. | Less prominent tessellation. | Prominent tessellation. |
| Inflorescence. | Racemes are shorter than those of the pollen parent. | Racemes are longer than those of 'SPCDW1513'. |
| Flower size. | Larger flowers than pollen parent. | Smaller flowers than 'SPCDW1513'. |
| Plant vigor. | Slower growing than the pollen parent. | Faster growing than 'SPCDW1513'. |
| Foliage. | Leaves are longer than those of the pollen parent. | Leaves are shorter than 'SPCDW1513'. |

Comparison with the most similar *Vanda* cultivar known to the inventor: Plants of the new cultivar 'SPCDW1513' are most similar to the cultivar, *Vanda* 'Blue Magic' (not patented in the United States; Netherlands Plant Breeders Right grand number 20716). A comparison of 'SPCDW1513' with *Vanda* 'Blue Magic' is described in Chart 3.

CHART 3

| Characteristic | 'SPCDW1513' | 'Blue Magic' |
|---|---|---|
| Leaf width. | 2.5 cm. | 2.8 cm. |
| Flower, vertical height. | 11.9 cm. | 11.5 cm. |
| Flower, diameter. | 11.8 cm. | 12.4 cm. |
| Petal color; upper surface, when opening. | Violet, near RHS 85C to 85D, with darker reticulate veining, near N88B. | Violet, near RHS 85C to 85D, with darker reticulate veining, near RHS N87A. |
| Petal color; lower surface, when opening. | Violet, near RHS 85C to 85D, with darker reticulate veining, near N88B. | Violet, near RHS 85C to 85D, with darker reticulate veining, near RHS N87A. |
| Petal color; upper surface, when fully open. | Violet, lighter than near RHS N87D, and fading darker, near RHS N87C to N87D. | Violet, lighter than near RHS N87D, and fading darker, near RHS N87C. |
| Petal color; lower surface, when fully open. | Violet, lighter than near RHS N87D, and fading darker, near RHS N87C. | Violet, near RHS N87D, and fading darker, near RHS N87C. |
| Venation color; lower petal surface, when fully open. | Violet, in between near RHS N87A and N88A and N88B. | Violet, in between near RHS N87A and N88A, yet closest to near N87A. |
| Labellum size. | 2.3 cm, on average. | 2.4 cm, on average. |
| Central lobe of labellum; color of the upper surface when fully open. | Violet, near RHS 86B, and fading to violet-blue at the top, near in between RHS N92B | Violet, near RHS 86A, and fading to violet at the top, near RHS N92C. to N92C. |
| Central lobe of labellum; | Violet, darker than near RHS 86A, and fading | Violet-purple, in between near RHS N89A and N92B, |

CHART 3-continued

| Characteristic | 'SPCDW1513' | 'Blue Magic' |
|---|---|---|
| color of the lower surface when fully open. | lighter towards the base, near RHS 86C to 86D. | and fading violet towards the base, near RHS N867A to N87B. |
| Dorsal sepal dimensions. | 6.2 cm long and 5.0 cm wide. | 6.4 cm long and 5.0 cm wide. |
| Lateral sepal dimensions, | 6.6 cm long and 6.0 cm wide. | 6.6 cm long and 6.2 cm wide. |
| Sepal color; upper surface, when opening. | Dorsal sepal and lateral sepals are violet, near RHS 85C to 85D, with darker reticulate veining near RHS N88B. | Lateral sepals and dorsal sepal are white, near RHS NN155D, and fading violet towards the top, near RHS 85C to 85D, with darker reticulate veining, near RHS N87B in dorsal sepal and near RHS N88B in lateral sepals. |
| Sepal color; lower surface, when opening. | Dorsal sepal and lateral sepals are violet, near RHS 85D, with darker reticulate veining, in between near RHS N87A and N88. | Dorsal sepal and lateral sepals are violet, near RHS 85C to 85D, with darker reticulate veining near RHS N87A in dorsal sepal and in between near RHS N87B and N88B in lateral sepals. |
| Sepal color; upper surface, when fully open. | Violet, lighter than near RHS N87D, and fading darker near RHS N87C to N87D. | White, near RHS NN155D, and fading violet towards the top, near RHS N87D. |

CHART 3-continued

| Characteristic | 'SPCDW1513' | 'Blue Magic' |
|---|---|---|
| Sepal color; lower surface, when fully open. | Violet, lighter than near RHS N87D, and fading darker near RHS N87C. | Dorsal sepal is purple-violet, near RHS N80D but lighter. Lateral sepals are violet, lighter than near RHSN87D, and fading darker, near RHS N87C. |
| Venation color; upper sepal surface, when fully open. | Dorsal sepal and lateral sepals are violet, in between near RHS N87A and N88A. | Dorsal sepal is violet, near RHS N87A. Lateral sepals are violet, in between near RHS N87A and N88A. |
| Venation color; lower sepal surface, when fully open. | Dorsal sepal and lateral sepals are violet, in between near RHS N87A and N88A and N88B. | Dorsal sepal is violet, in between near RHS N87A and N88A. Lateral sepals are violet, in between near RHS N87A and N88A; closest to N88A. |
| Petal and sepal aspect. | Flat. | Somewhat twisted or spiraled in a propeller-like fashion. |

That which is claimed is:

1. A new and distinct variety of *Vanda* plant named 'SPCDW1513', substantially as described and illustrated herein.

* * * * *